US 6,413,243 B1

(12) United States Patent
Geist

(10) Patent No.: US 6,413,243 B1
(45) Date of Patent: Jul. 2, 2002

(54) APPARATUS FOR COVERING A USED SYRINGE NEEDLE

(75) Inventor: Leroy D. Geist, Parker, CO (US)

(73) Assignee: Vital Signs, Inc., Totawa, NJ (US)

(*) Notice: Subject to any disclaimer, the term of this patent is extended or adjusted under 35 U.S.C. 154(b) by 0 days.

(21) Appl. No.: 09/510,122

(22) Filed: Feb. 21, 2000

(51) Int. Cl.$^7$ .............................................. A61M 5/32
(52) U.S. Cl. ...................... 604/192; 604/110; 604/263
(58) Field of Search ................................ 604/110, 187, 604/192, 263

(56) References Cited

U.S. PATENT DOCUMENTS

| | | | |
|---|---|---|---|
| 4,820,277 A | 4/1989 | Norelli | 604/192 |
| 4,850,976 A | 7/1989 | Heinrich et al. | 604/192 |
| 4,872,552 A | 10/1989 | Unger | 206/365 |
| 4,883,469 A | 11/1989 | Glazier | 604/192 |
| 4,909,791 A | 3/1990 | Norelli | 604/192 |
| 4,909,792 A | 3/1990 | Norelli | 604/192 |
| 4,944,731 A | 7/1990 | Cole | 604/192 |
| 4,982,842 A | 1/1991 | Hollister | 206/365 |
| 5,135,508 A | 8/1992 | Vernamonti | 604/192 |
| 5,135,509 A | 8/1992 | Olliffe | 604/192 |
| 5,139,489 A | 8/1992 | Hollister | 604/192 |
| 5,151,089 A | 9/1992 | Kirk, III et al. | 604/192 |
| 5,154,285 A | 10/1992 | Hollister | 206/365 |
| 5,188,611 A | 2/1993 | Orgain | 604/192 |
| 5,232,455 A | 8/1993 | Hollister | 604/192 |
| 5,242,417 A | 9/1993 | Paudler | 604/192 |
| 5,312,368 A | 5/1994 | Haynes | 604/192 |
| 5,342,322 A * | 8/1994 | Nathan et al. | 604/192 |
| 5,405,332 A | 4/1995 | Opalek | 604/192 |
| 5,423,765 A | 6/1995 | Hollister | 604/192 |
| 5,445,619 A | 8/1995 | Burns | 604/192 |
| 5,486,163 A | 1/1996 | Haynes | 604/192 |
| 5,490,841 A | 2/1996 | Landis | 604/110 |
| 5,509,907 A | 4/1996 | Bevilacqua | 604/263 |
| 5,599,313 A | 2/1997 | Gyure et al. | 604/192 |
| 5,599,318 A | 2/1997 | Sweeney et al. | 604/263 |
| 5,603,699 A | 2/1997 | Shine | 604/110 |
| 5,643,219 A | 7/1997 | Burns | 604/192 |
| 5,662,617 A | 9/1997 | Odell et al. | 604/192 |
| 5,669,889 A | 9/1997 | Gyure et al. | 604/263 |
| 5,681,295 A | 10/1997 | Gyure et al. | 604/263 |
| 5,746,726 A | 5/1998 | Sweeney et al. | 604/263 |
| 5,807,351 A | 9/1998 | Kashmer | 604/263 |
| 5,868,716 A | 2/1999 | Sweeney et al. | 604/263 |
| 5,891,103 A | 4/1999 | Burns | 604/192 |
| 5,919,165 A | 7/1999 | Benson | 604/110 |
| 6,159,184 A * | 12/2000 | Perez et al. | 604/192 |
| 6,319,233 B1 * | 11/2001 | Jansen et al. | 604/192 |

FOREIGN PATENT DOCUMENTS

| | | |
|---|---|---|
| EP | 0 352 008 A2 | 1/1990 |
| EP | 0 566 631 B1 | 10/1993 |
| EP | 0 623 358 A2 | 11/1994 |
| EP | 0 626 924 B1 | 12/1994 |
| WO | WO 98/11928 | 3/1998 |

* cited by examiner

Primary Examiner—J. Casimer Jacyna
(74) Attorney, Agent, or Firm—R. Gale Rhodes, Jr.

(57) ABSTRACT

Apparatus for covering a used hypodermic syringe needle including a base, a pair of covers mounted movably to the base and at least one latching member mounted on the base, the covers are for being moved into a closed position covering the used syringe needle, the covers are provided with engaging members making the movement of each cover dependent on the movement of the other cover, and the latching member is for engaging the engaging members to lock both covers in the closed position. In the preferred embodiment a pair of latching members are mounted on the base and each latching member is for independently engaging the engaging members to cause either or both of the latching members to lock both of the covers in the closed position.

20 Claims, 8 Drawing Sheets

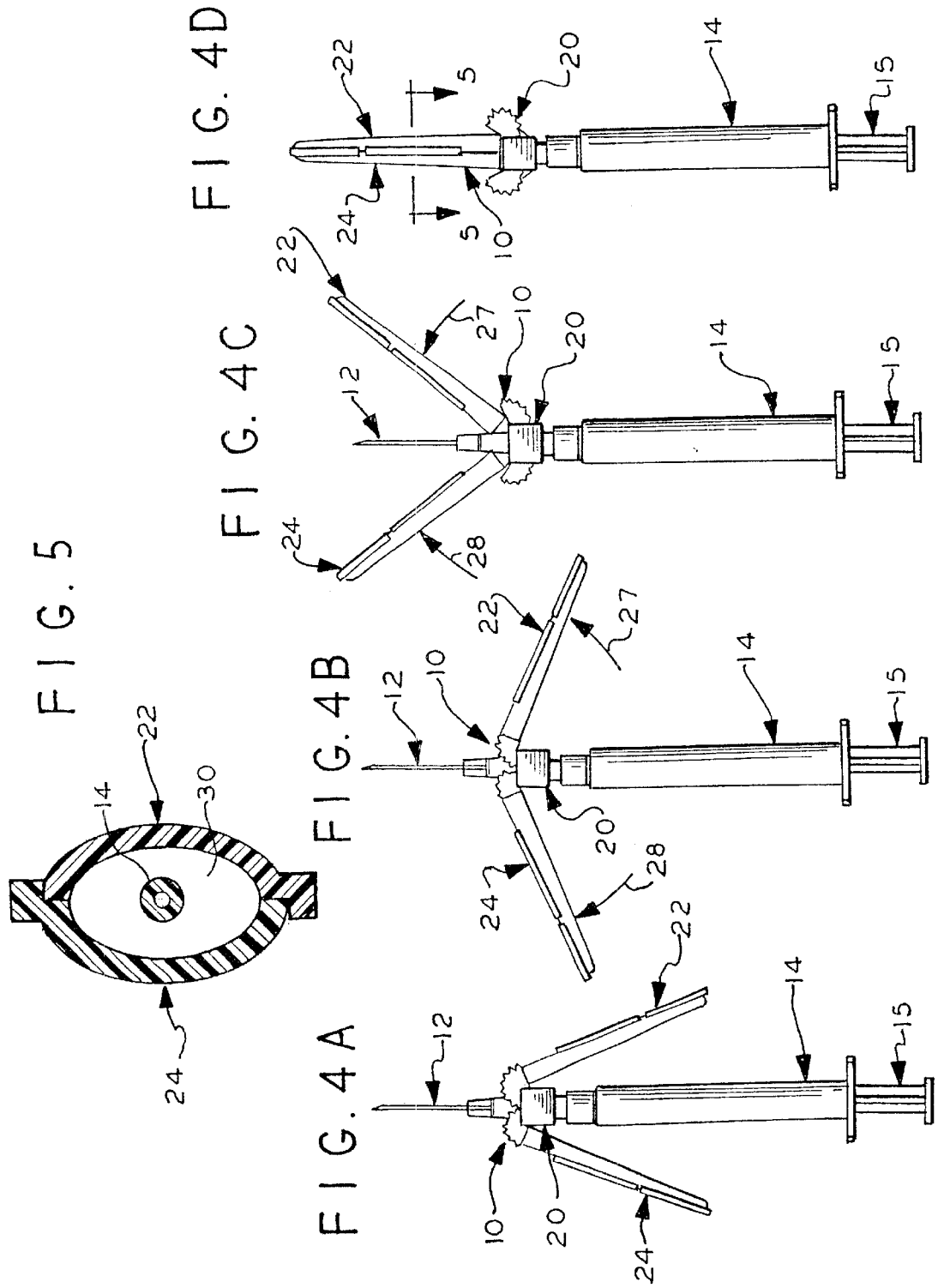

APPARATUS FOR COVERING A USED SYRINGE NEEDLE

BACKGROUND OF THE INVENTION

This invention relates to apparatus for covering a used hypodermic syringe needle.

Accidental skin puncture by a used hypodermic syringe needle places health care providers, such as doctors, nurses, medical assistants, and others, at grave risk from exposure to highly infectious diseases, some of which have no presently known cure or which are very difficult to treat, for example, the AIDS virus and hepatitis.

Numerous apparatus are known to the art for covering a used syringe needle to prevent accidental skin puncture from the needle.

However, it is believed that there still exists a need in the art for new and improved apparatus for covering a used hypodermic syringe needle whose components are relatively inexpensive to manufacture, relatively inexpensive to assemble, and which apparatus can be sold relatively inexpensively.

SUMMARY OF THE INVENTION

It is the object of the present invention to satisfy the foregoing need in the art.

Apparatus for covering a used hypodermic syringe needle and satisfying the foregoing need may include a base, a pair of covers mounted movably to the base, and at least one latching member mounted to the base. The covers are for being moved into a closed position over the needle. The covers are engaged making the movement of each cover dependent on the movement of the other cover, and the latching member is for engaging at least one of the covers to lock both of the covers in the closed position. In the preferred embodiment, a pair of latching members are mounted to the base and the pair of latching members independently engage the covers to cause either or both of the latching members to lock both of the covers in the closed position.

DESCRIPTION OF THE DRAWINGS

FIGS. 4A–4D are sequential elevational views illustrating the manner of use of the apparatus of the present invention;

FIG. 5 is an enlarged transverse cross-sectional view taken generally along the line 5—5 in FIG. 4D in the direction of the arrows;

DESCRIPTION OF THE PREFERRED EMBODIMENT

Figure 1:
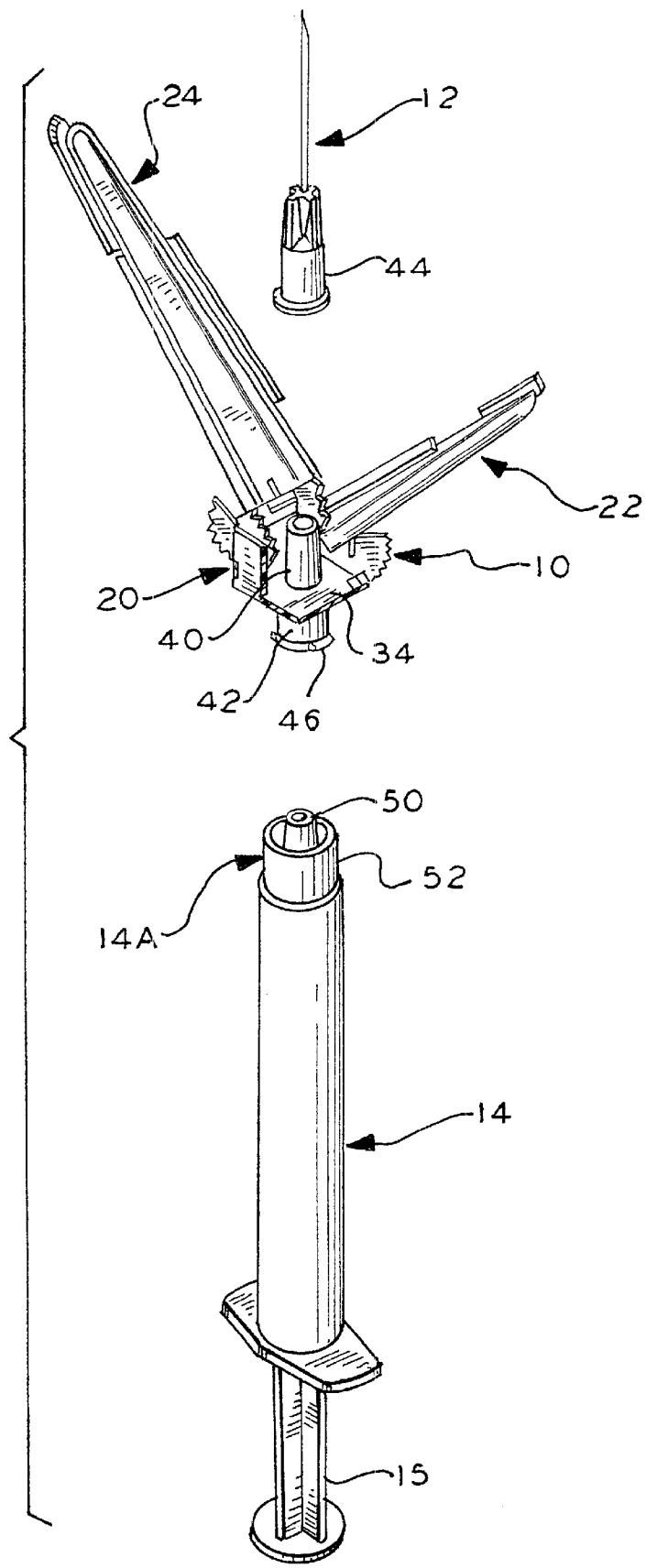
FIG. 1 is an exploded view, in perspective, showing the preferred embodiment of the apparatus of the present invention for covering a used hypodermic syringe needle with the covers shown in the open position, also shown in this FIG. 1 are a hypodermic syringe needle and a syringe comprised of a syringe barrel and plunger.
Figure 2:
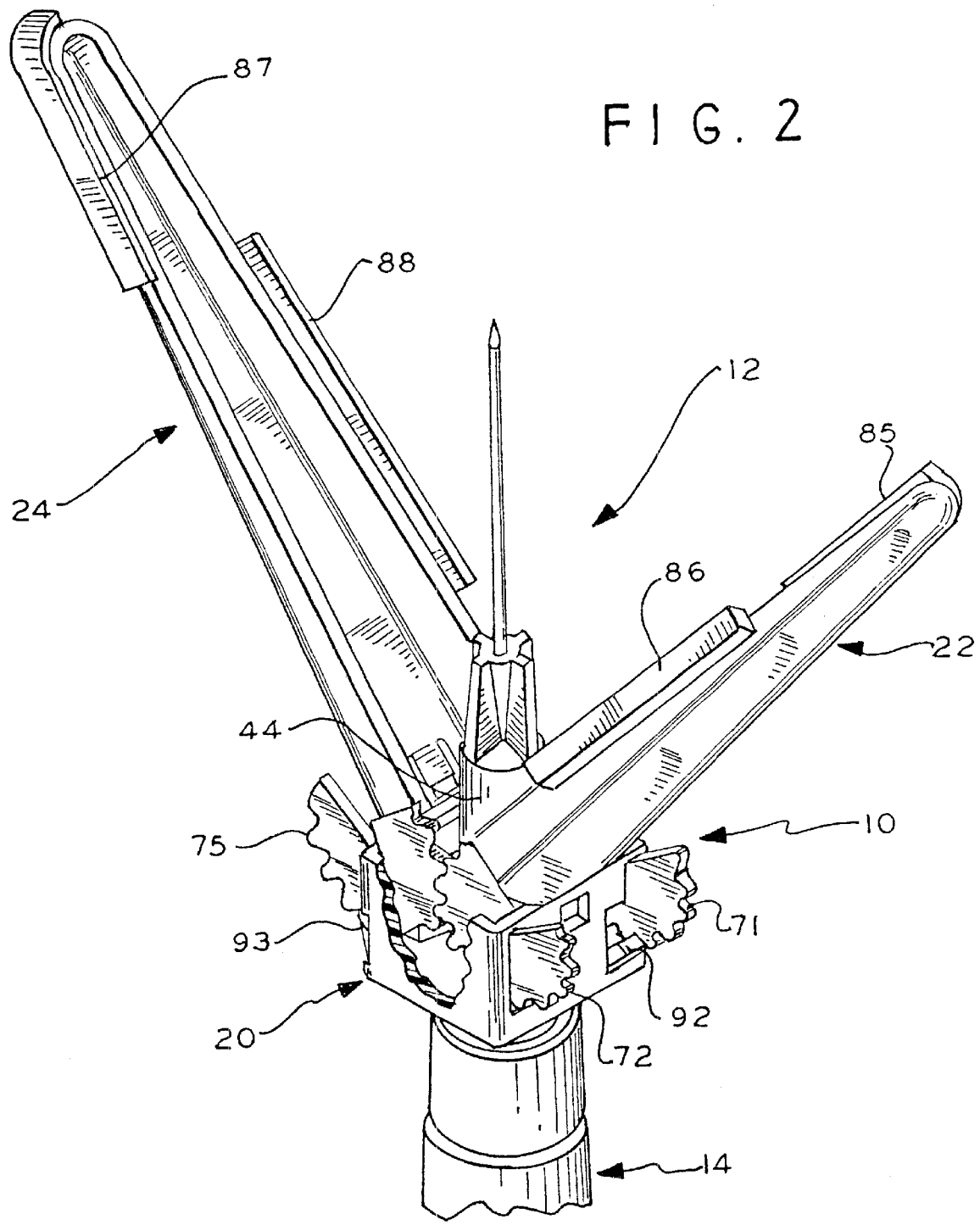
FIG. 2 is a partial perspective view showing the hypodermic syringe needle and the syringe mounted to the apparatus of the present invention.
Figure 3:
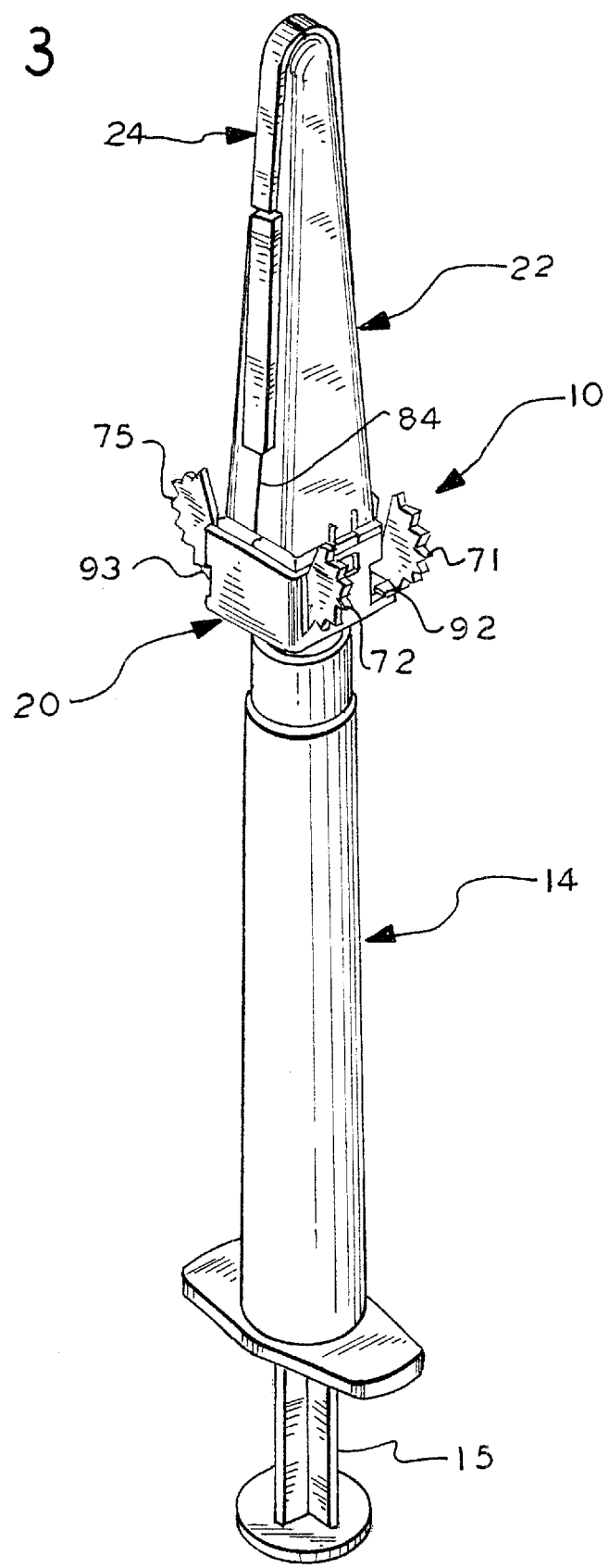
FIG. 3 is a perspective view of the apparatus of the present invention with the covers shown in the closed position to cover a used hypodermic syringe needle.

Referring to FIGS. 1–3 of the drawings, and in particular to FIG. 1, there is shown apparatus for covering a used hypodermic syringe needle embodying the present invention and indicated by general numerical designation 10. It will be understood that while the terms hypodermic syringe needle, hypodermic needle and syringe needle are used in the art, for convenience of presentation, the term syringe needle will be used hereinafter in the appended claims; further the apparatus of the present invention sometimes may be referred to hereinbelow as used syringe needle covering apparatus. Also shown in these FIGS. are a syringe needle indicated by general numerical designation 12 and a syringe indicated by general numerical designation 14. The syringe needle 12 and syringe 14 are of the type known to the art for injecting a patient with a liquid such as a liquid medication or for drawing a blood sample from a patient. After injection or the taking of a blood sample, the syringe needle 12 is withdrawn from the patient by the health care provider and it is at this time that either the health care provider, or another person, is at risk of having his/her skin accidentally punctured by the used syringe needle whereby an infectious disease, of the type noted above, can be transferred from the patient to the health care provider or another person.

Referring again to the present invention and to FIGS. 1–3, it will be generally understood that the used syringe needle covering apparatus 10 of the present invention includes a base or body indicated by general numerical designation 20 and a pair of covers mounted pivotally on the base and being indicated respectively by general numerical designations 22 and 24. As will be generally understood from FIG. 2, and as described in detail below, the covers 22 and 24 are provided with engaged gears making the pivoting movement of each cover dependent on the pivoting movement of the other cover. In FIGS. 2 and 3, the syringe needle 12 and syringe 14 are shown mounted to the used syringe needle covering apparatus 10 of the present invention and, it will be understood, that the manner in which the apparatus 10 and syringe needle 12 and syringe 14 are mounted together is set forth in detail below.

Before describing the detailed structure of the present invention, a general understanding of the function and operation of the used syringe needle covering apparatus of the present invention will be presented in connection with the sequence drawings FIGS. 4A–4D. FIG. 4A shows the used syringe needle covering apparatus 10 of the present invention mounted to a syringe needle 12 and a syringe 14; FIG. 4A also shows the condition or state in which the health care provider receives such apparatus, syringe needle and syringe after they are removed from the packaging in which they are packaged at the factory. While not shown in FIG. 4A, it will be understood that as known to the art and as is conventional, the syringe needle 12 would come covered with a removable protective sleeve (not shown) which is removed to place the syringe needle in the exposed condition shown in FIG. 4A. With the apparatus 10 of the present invention in place as shown in FIG. 4A, the syringe 14 and syringe needle 12 would be used by the health care provider, as described above, to take a blood sample from a patient or to inject a patient with a liquid medication and, after the syringe needle has been used, the syringe needle 12 would be withdrawn from the patient and the health care provider, for example would apply an upwardly acting force to one of the respective covers 22 or 24, as indicated by the arrows 27 and 28 in FIGS. 4B and 4C, to pivot the covers upwardly towards each other and towards the used syringe needle 12 until the covers 22 and 24 are pivoted together in a closed position over the used syringe needle 12 as shown in FIG. 4D to cover the needle and prevent the used syringe needle from causing any accidental skin puncture of the health care provider's skin, or the skin of another person. From FIG. 5, it will be understood that the covers 22 and 24 are generally semi-circular, or generally semi-rectangular, in transverse cross-section, and upon being closed, as shown in FIG. 4D, the covers 22 and 24 provide a generally longitudinally extending cavity, indicated by numerical designation 30 in FIG. 5, which accommodates the used syringe needle 12; the covers 22 and 24 enclose or surround the syringe needle 12 thereby isolating the health care provider or other person from the used needle and fluid leakage therefrom. Further the covers 22 and 24 are spaced from, or do not touch, the syringe needle thereby further minimizing the possibility of perforation of the covers by the used needle point.

Figure 6:
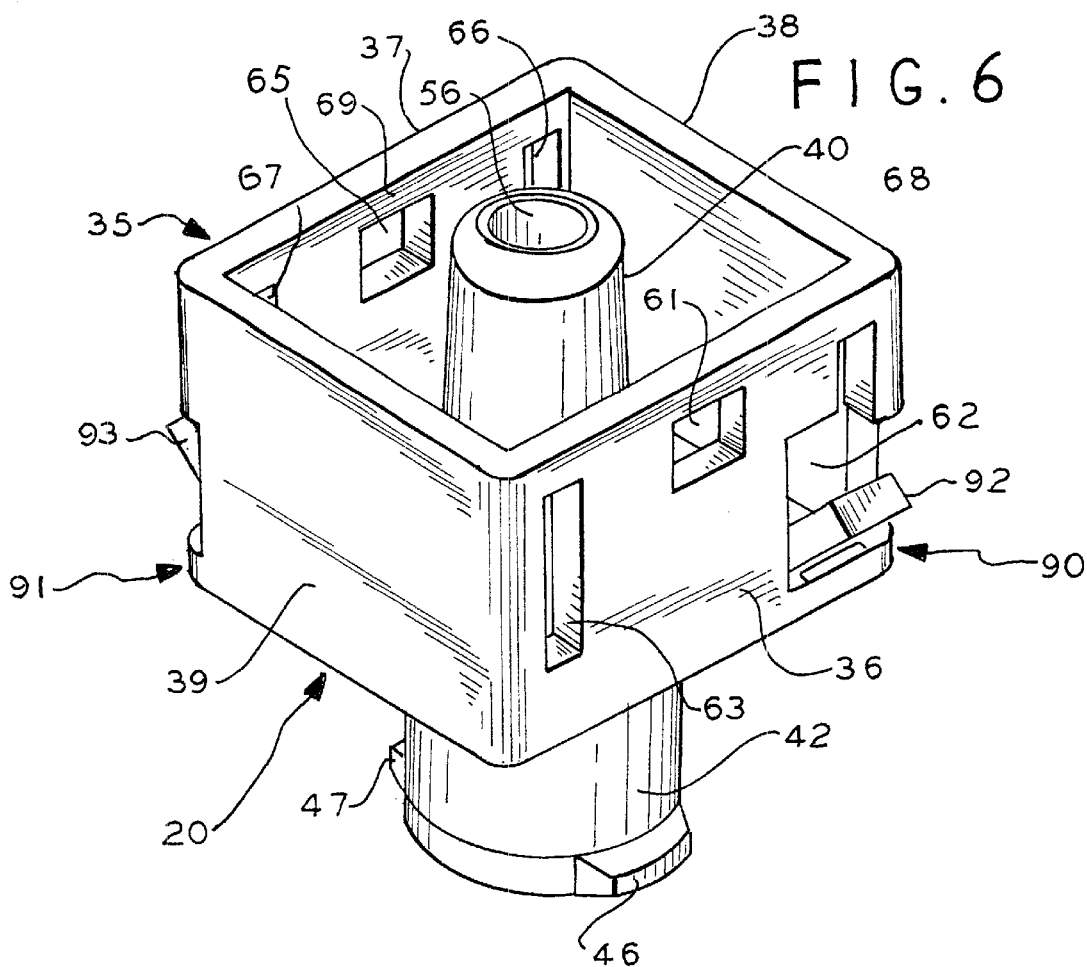
FIG. 6 is a perspective view of the base of the apparatus of the present invention.
Figure 7:
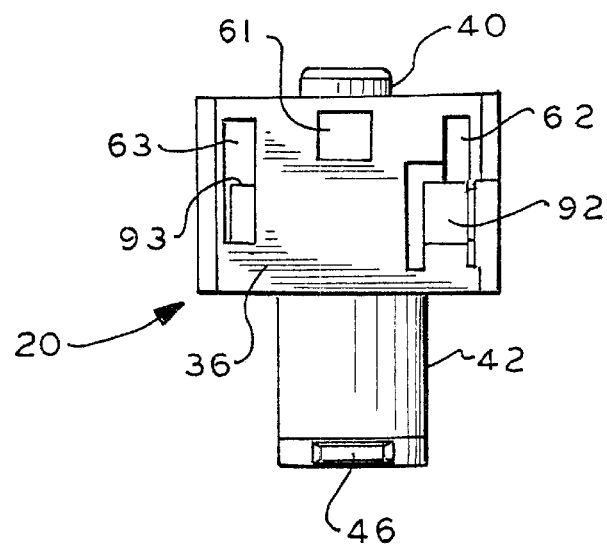
FIG. 7 is an elevational view of a wall shown in FIG. 6.
Figure 8:
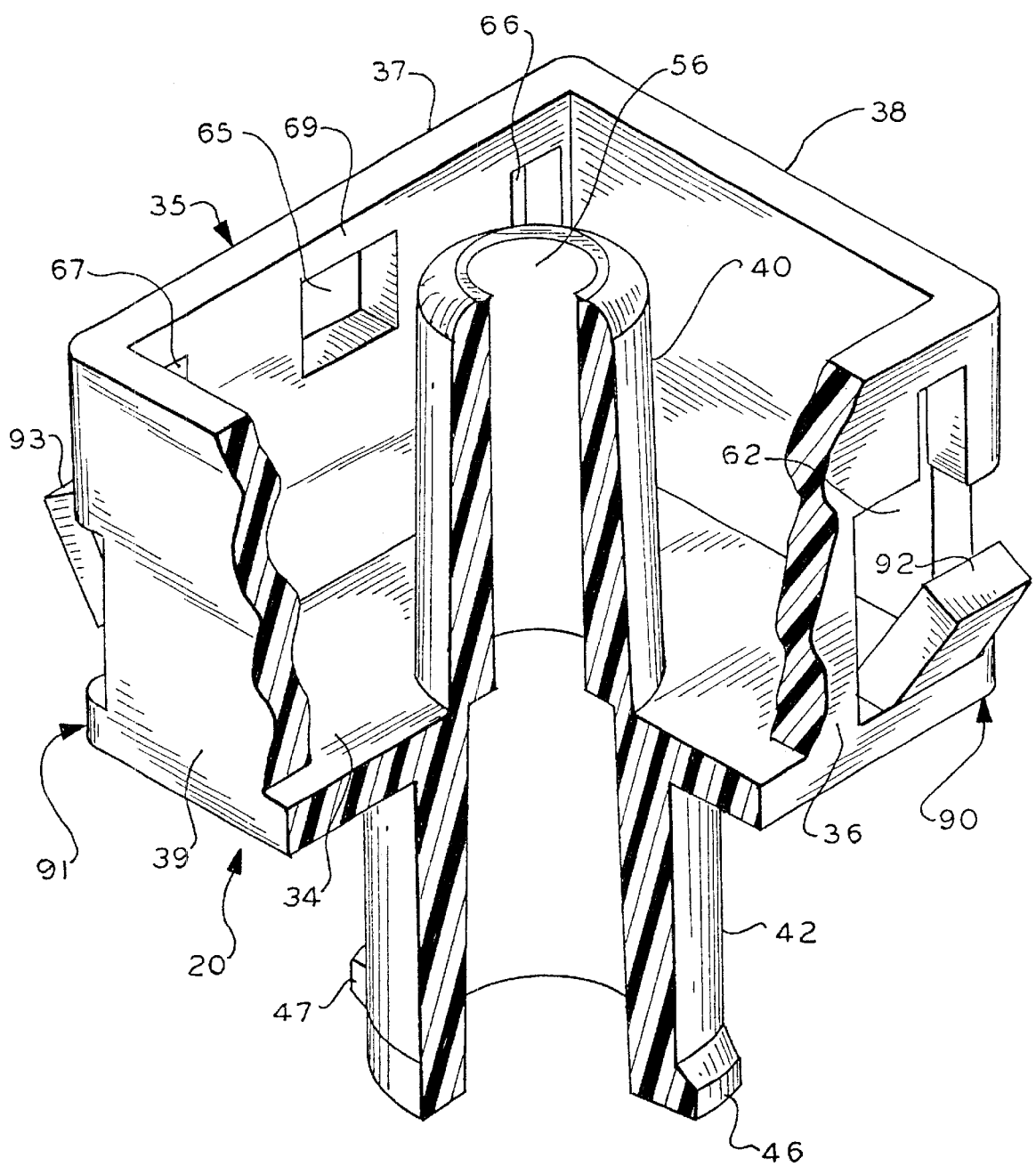
FIG. 8 is a view similar to FIG. 6 but having portions broken away to show the internal liquid passageway through the base and luer connectors of the present invention.

Referring now to FIGS. 6, 7 and 8 and to the detailed structure of the base 20, the base 20 comprises a generally rectangular shell as shown in FIGS. 6 and 8 and which shell includes a generally rectangular bottom wall or base member 34 (note particularly FIG. 8) which is circumscribed by an upwardly extending rectangular wall indicated by general numerical designation 35. Rectangular wall 35 includes a pair of opposed side walls 36 and 37 and a pair of opposed side walls 38 and 39. The rectangular base member 34, note particularly FIG. 8, includes a generally central portion (not numbered) and extending upwardly from the central portion of the base member 34 and within the rectangular wall 35 is a generally cylindrical or tubular member 40 and extending downwardly from the central portion of the base member 34 and opposite the tubular member 40 is a generally cylindrical or tubular member 42. It will be understood that the terms upwardly and downwardly as used herein to describe the components of the present invention are used for convenience of reference and are merely used as relative terms with regard to the orientations of components as shown in the patent drawings. It will be further understood that the used syringe needle covering apparatus of the present invention may be oriented in many orientations or positions other than those shown in the drawings.

Referring again to the tubular portion 40, FIGS. 6 and 8, it will be understood that the upwardly extending tubular portion 40 is shaped or formed as a tapered male luer connector. The syringe needle 12, FIG. 1, in the manner known to the art, is provided with an internally tapered female luer connector 44 (FIG. 1). Accordingly, it will be understood that, to mount the syringe needle 12 (FIG. 1) to the apparatus 10 of the present invention, the tapered male luer connector 40 of the present invention is for slidingly and wedgedly engaging the syringe needle female luer connector 44 (FIG. 1) of the syringe needle 12 in a leak-proof connection referred to in the art as a slip-fit luer connection. In FIG. 2, the needle syringe female luer connector 44 is shown slip-fitted over the male luer connector 40 which is not shown in FIG. 2 because it is covered by the female luer connector 44.

From FIGS. 6 and 8, it will be understood that the downwardly extending tubular portion 42 is shaped or formed as an inwardly tapered female luer connector which is provided at its outer portion with a pair of outwardly extending lugs 46 and 47. The syringe 14, as shown in FIG. 1 and as is known to the art, is provided at its upper end 14A with a centrally disposed tapered male luer connector 50 spaced from and encircled by an internally threaded collar 52. Accordingly, it will be understood that the inwardly tapered female luer connector 42 (FIGS. 6 and 8) provided on the base 20 is for engaging the tapered male connector 50 provided on the syringe 14 in a leak-proof slip-fit connection and that, upon relative rotational movement between the syringe 14 and body 20, the lugs 46 and 47 of the tapered male luer connector 42 are for threadedly engaging the internally threaded collar 52 (FIG. 1) provided on the syringe end 14A in a luer connection referred to in the art as a twisting or locking-fitting luer connection. In FIGS. 2 and 3, the syringe 14 is shown connected to the body 20 of the used syringe needle cover apparatus 10 of the present invention, although the respective luer connectors 50 and 52 are not shown in FIG. 2.

Referring again to FIG. 8, it will be understood that an internal liquid passageway 56 extends through the upper luer connector 40, the base member 34, and the lower luer connector 42. Liquid passageway 56 places the luers 40 and 42 in fluid communication to permit blood samples to be taken or to permit the patient to be injected with a liquid medication.

Referring again to FIGS. 6 and 7, it will be understood that opposed pair of walls 36 and 37 of the base 20 are provided with pluralities of openings. As shown in FIGS. 6 and 7, wall 36 is provided with a rectangular central opening 61 and a pair of lateral openings 62 and 63 provided on either side of the central opening 61. Opposed wall 37, FIG. 6, is provided with a rectangular central opening 65 and a pair of generally rectangular lateral openings 66 and 67 provided on either side of the central opening 65. It will be understood that the respective upper portions 68 and 69, note particularly FIG. 6, of the pair of opposed shell walls 36 and 37 provide axles about which the respective covers 22 and 24 pivot, as described above with regard to FIGS. 4B and 4C, to close over the used syringe needle 12.

Figure 9:
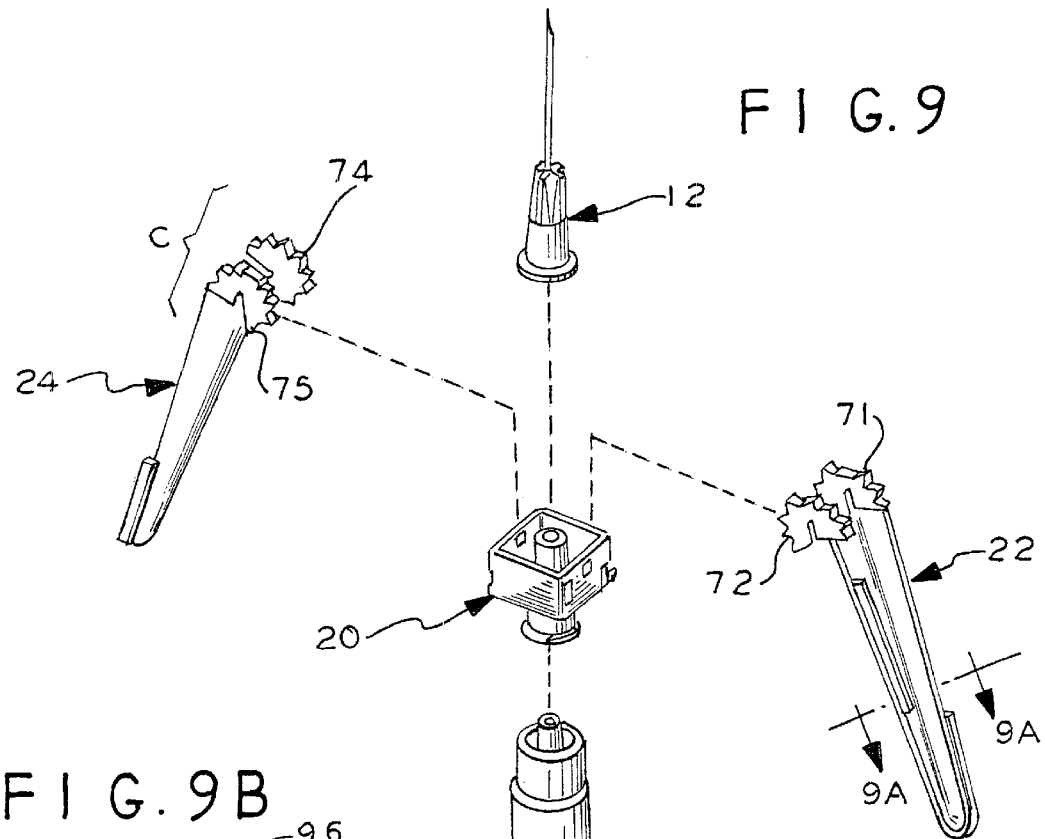
FIG. 9 is an exploded view including dashed lines indicating the manner of assembly of the components comprising the apparatus of the present invention, this FIG. also shows a hypodermic syringe needle and a syringe.
Figure 9B:
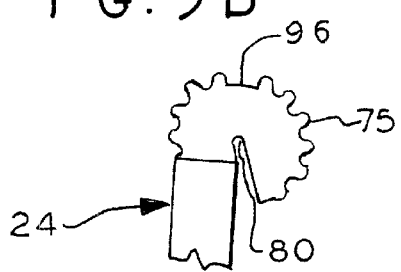
FIG. 9B is an enlarged view of the upper portion of a cover gear sector shown in the upper leftward portion of FIG. 9.
Figure 9C:
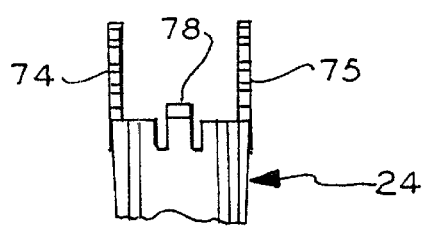
FIG. 9C is a partial plan view of the bracketed inner portion of the leftward cover shown in FIG. 9, the bracketed portion is identified in FIG. 9 by the bracket C.
Figure 9A:
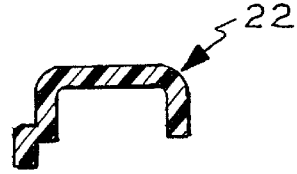
FIG. 9A is a transverse cross-sectional view taken generally along the line 9—9 in FIG. 9 in the direction of the arrows.

The detailed structure of the covers 22 and 24 is best seen in FIG. 9. As viewed in FIG. 9, and relative to the base 20, the outer portions of the covers 22 and 24 are generally triangular and taper inwardly outwardly. As noted generally above with regard to FIG. 5, the covers, note representative cover 22, are generally semi-circular in transverse cross-section as shown in FIG. 9A. The inner portions of the covers 22 and 24, relative to the base, are provided, respectively, with pairs of spaced apart and generally parallel gear sectors 71 and 72 and 74 and 75 which gear sectors include gear teeth as shown. As will be understood in particular from representative cover 24 as shown in FIG. 9C, a cantilever tab 78 is provided on the inner portions of the cover and disposed between the gear sectors, e.g. between representative gear sectors 74 and 75. The gear sectors, note representative gear sector 24 shown in FIG. 9B, are provided with inwardly extending radial slots 80 for receiving the axles 68 and 69 (FIG. 6) to mount the covers 22 and 24 pivotally to the base 20.

Referring further to FIGS. 6 and 8, the body 20, particularly the pair of opposed walls 36 and 37, includes diagonally disposed lower portions indicated respectively by general numerical designations 90 and 91. A pair of diagonally disposed and angularly inclined latching members 92 and 93 are provided respectively on the diagonal portions 90 and 91 of the body 20 for engaging one gear sector of each pair of gear sectors 71 and 72 and 74 and 75 shown in FIG. 9. More particularly, note FIG. 2, latching member 92 is for engaging the teeth of gear sector 71 of the pair of gear sectors 71 and 72 provided on cover 22, and latching member 93 is for engaging the teeth provided on gear sector 75 of the pair of gear sectors 74 and 75 (FIG. 9) provided on cover 24. Thus, it will be generally understood in accordance with the teachings of the present invention that the latching members 92 and 93 engage the respective pairs of gear sectors 71 and 72 and 74 and 75 independently, and it will be more particularly understood that the pair of latching members independently engage one gear sector of a pair of such gear sectors.

Figure 10:
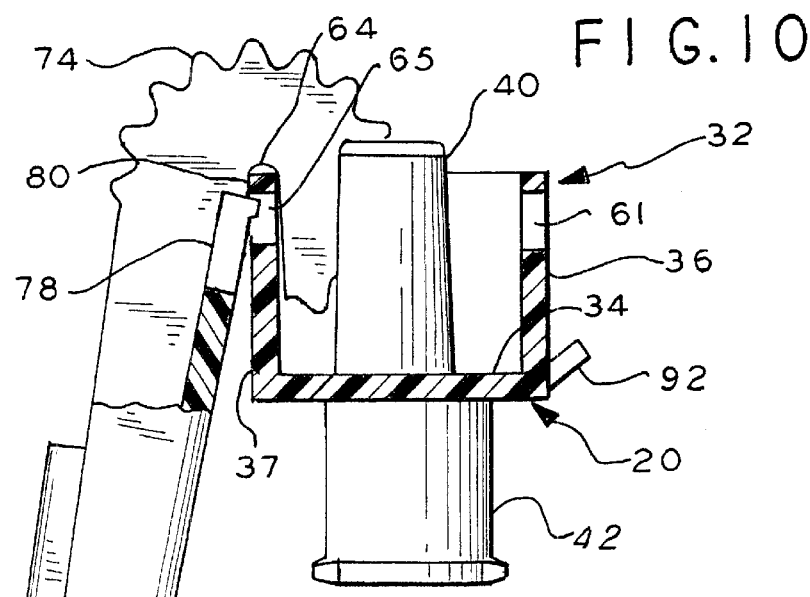
FIG. 10 is a vertical elevational view, partially in cross-section, illustrating the snap-fit connection of a representative cover to the base of the present invention.

It will be further understood that the cantilever tabs 78 provided on the covers 22 and 24 and the central openings 61 and 65 (FIG. 7) provided in the respective opposed walls 36 and 37 of the body 20 provide snap-fit connecting means for assembling or snap-fitting the covers 22 and 24 to the base 20. More particularly, the covers 22 and 24 are mounted or assembled to the base 20 by placing the covers on the base 20, as shown in FIG. 10 with regard to representative cover 24, with the radial slots 80 of the gear sectors receiving the axles 68 and 69 (FIG. 6) provided on the base 20; representative radial slot 80 of cover 24 is shown receiving the axle 69 in FIG. 10. As the covers 22 and 24 are assembled to the base 20, the cantilever tabs 78 provided between the pairs of gear sectors (FIG. 9C) snap into the central openings 61 and 65 (FIG. 6) and snap-fit the covers to the base. Upon the cover tabs 78 being inserted, snapped, in the respective central openings 61 and 65 (FIG. 6), the tabs restrain the covers against lateral movement with respect to the base 20 and restrict the covers to pivoting movement with regard to the base. As the person assembling the apparatus 10 of the present invention rotates the covers 22 and 24 upwardly from the position shown in FIG. 10 for representative cover 24 into the positions shown for the covers in FIG. 4A, the pairs of gear sectors 71 and 72 and 74 and 75 provided on the covers engage and the pairs of gear sectors 71 and 72 provided cover 22 extend outwardly through the lateral slots 62 and 63 (FIG. 6) provided in wall 38, and the pairs of gear sectors 74 and 75 provided on the cover 24 extend outwardly through the lateral slots 66 and 67 (FIG. 7) provided in the wall 37. The engagement of gear sector 72 provided on the cover 22 with the gear sector 75 provided on cover 24 is shown in FIG. 2, and although not shown in FIG. 2, it will be understood that gear sector 71 provided on cover 22 is in engagement with the gear sector 74 (FIG. 9) provided on the gear cover 24. Thus, as noted generally above, due to the engagement of the pairs of gear sectors 71 and 72 and 74 and 75, the pivoting movement of each cover is dependent on the pivoting movement of the other cover whereby the closing of the covers over the used syringe needle as illustrated in FIGS. 4B–4D and described above can be performed by the health care provider by applying upwardly acting force to either or both covers. Thereafter, as described above with regard to sequence FIGS. 4B–4D, the apparatus of the present invention may be used to cover a used syringe needle.

Figure 11:
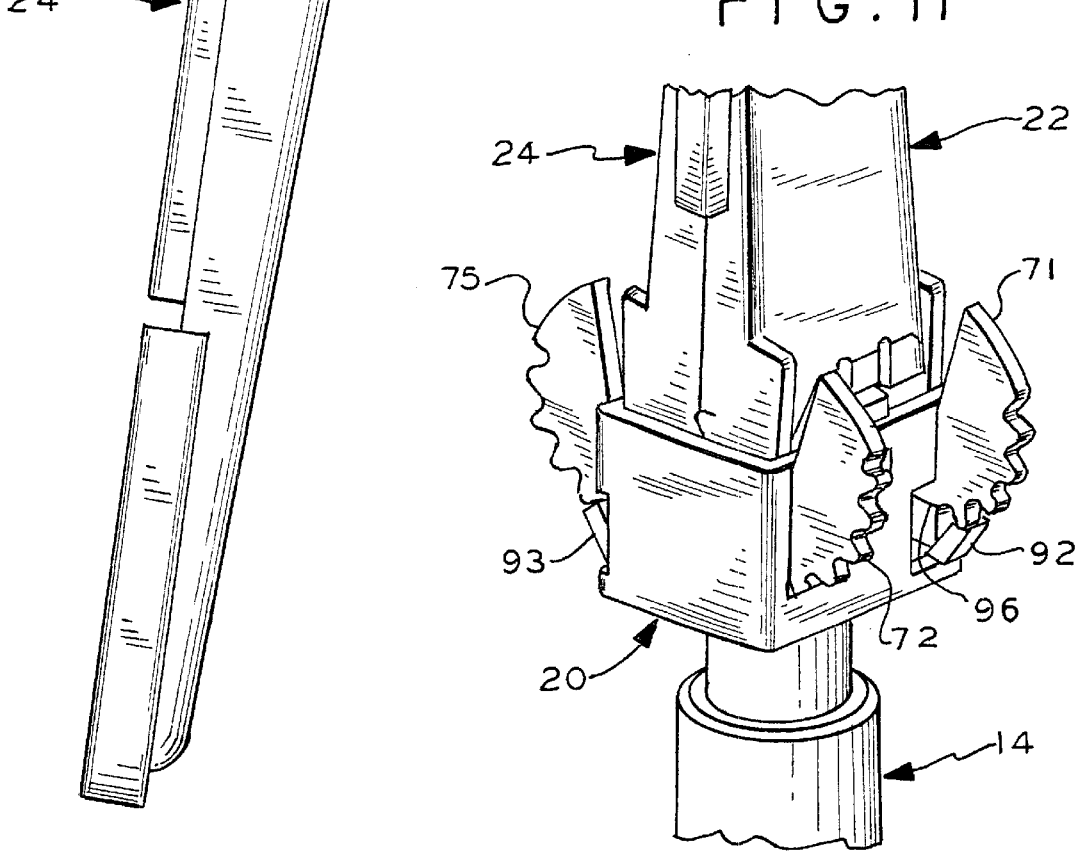
FIG. 11 is a partial perspective view illustrating the locking of the covers in the closed position covering a used hypodermic syringe needle.

In accordance with the further teachings of the present invention, it will be understood from FIGS. 2, 4B–4D and 6 that as the covers 22 and 24 are pivoted upwardly as shown in FIGS. 4B and 4C, the latching members 92 and 93, due to their angular inclination engage the teeth of the respective gear sectors 71 and 75 (FIG. 2) and prevent these gear sectors from rotating downwardly, opposite to the direction of the arrows 27 and 28 in FIGS. 4B and 4C, and thereby provide the covers 22 and 24 with, or limit the covers to, uni-directional upward pivoting movement towards each other into the closed used needle covering position shown in FIG. 4D. It will be still further understood that upon the covers 22 and 24 being pivoted into their closed position shown in FIG. 4D covering the used syringe needle, the angularly inclined latches 92 and 93, due to their engagement with the gear sectors 71 and 75, lock the covers in their closed position. To enhance this locking action, and to assure that the latching members reside in an indentation between the teeth on the gear sectors 71 and 75, the gear sectors 71 and 75 are provided with toothless gear slots or sectors greater in width than the width of the teeth provided on such gear sectors; this is illustrated in detail in FIG. 9B with regard to representative gear sector 75 of cover 24 shown to be provided with toothless gear slot or sector 96. This is further illustrated in FIG. 11 with regard to gear sector 71, latching member 92 and toothless gear slot or sector 96. It will be further understood that in accordance with the further teachings of the present invention, since the latching members 92 and 93 engage the respective pairs of gear sectors 71 and 72 and 74 and 75 independently, and since the pairs of gear sectors are engaged making the pivoting movement of each cover dependent on the pivoting movement of the other cover, either or both of the latching members 92 and 93 will lock the covers in the closed position covering the used syringe needle. Thus if either latching member 92 or 93 is broken off from the body 20, or becomes dysfunctional, such as by becoming disengaged from its associated gear sector, the other latching member will lock the covers 22 and 24 in the closed position covering the used syringe needle. Also in the absence or dysfunction of either latching member the other or remaining latching member will provide the covers with, or limit the covers to, unidirectional pivoting movement towards each other into the closed position to cover the used syringe needle.

Referring again to FIGS. 1 and 3, and in particular to FIG. 3, it will be understood that the covers 22 and 24 close over the used syringe needle 12 (FIG. 1) is a line engagement, note the line 84 in FIG. 3. To provide further covering to the used syringe needle 12, the covers 22 and 24, note FIG. 2, are provided, respectively, with alternately disposed inwardly extending flanges 85 and 86 and 87 and 88 which substantially cover the straight line engagement 84 (FIG. 3) between the covers when the covers are pivoted closed over the used syringe needle 12 as shown in FIG. 2.

Referring again generally to FIGS. 2 and 11, it will be understood that it is within the contemplation of the present invention that instead of the latching members 92 and 93 being diagonally disposed, both latching members may be mounted on one side of the base 20 or extend outwardly from one side wall such as, for example, side wall 36 shown in FIG. 8. In addition, it will be understood that due to the gear engagement between the covers 22 and 24 making their pivoting movement dependent, that it is within the further contemplation of the present invention that the apparatus 10 include one, two or four latching members for providing the covers with unidirectional pivoting movement and for locking or latching such covers in the closed position surrounding the used syringe needle.

The body 20 and covers 22 and 24 of the preferred embodiment 10 of the present invention may be made from a suitable thermoplastic material, such as for example polypropylene, and may be made by a suitable manufacturing technique, such as for example injection molding. It will be understood from FIG. 9 that the covers 22 and 24 are identical in shape or configuration and thus may be molded in a single mold. Referring again to FIG. 6, it will be understood that the body 20 may be molded with the latching members 92 and 93 molded flush with the respective opposed walls 36 and 37 thereby simplifying the mold for the body 20. As the pairs of gear sectors 71 and 72 and 74 and 75 are mounted to the body 20 as described above, the gear sectors 71 and 75 push the respective latching members outwardly into the angular dispositions shown in FIGS. 6 and 8. It will be understood that the latching members are shown inclined and extending outwardly in FIGS. 6 and 8 for convenience of teaching the present invention.

It will be understood by those skilled in the art that many modifications and variations may be made in the present invention without departing from the spirit and the scope thereof.

What is claimed is:

1. Apparatus for covering a used syringe needle, comprising:
    base means;
    a pair of covers mounted movably to said base means and for being moved into a closed position covering the used syringe needle, said covers provided with engaging means making the movement of each cover dependent on the movement of the other cover; and
    a pair of latching means mounted on said base means and each latching means for independently engaging said engaging means to cause either or both of said latching means to lock both of said covers in said closed position.

2. The apparatus according to claim 1 wherein said engaging means are gear means.

3. The apparatus according to claim 2 wherein said pair of covers are mounted pivotally to said base means for pivoting movement towards each other into said closed position; wherein said gear means comprise at least one gear sector provided on each of said covers, said gear sectors being engaged to cause the pivoting movement of each cover to be dependent on the pivoting movement of the other cover.

4. The apparatus of claim 3 wherein said pair of latching means comprise a pair of diagonally disposed and angularly inclined latching members, each latching member engaging a gear sector provided on a different one of said covers to lock both of said covers in said closed position; and wherein said latching members impart uni-directional pivoting movement to said covers.

5. Apparatus according to claim 3 wherein said base means comprises a shell providing opposed axle portions about which said covers are mounted for pivoting movement towards each other.

6. The apparatus according to claim 5 wherein said base means and said covers are provided with cooperative snap-fit means for snap-fitting said covers to said base means.

7. The apparatus according to claim 5 wherein said base means comprises a generally rectangular shell including a generally rectangular base member circumscribed by a rectangular wall including two pairs of opposed walls, and wherein one pair of opposed walls of said two pairs of opposed walls are provided with said axle portions and wherein said axle portions are disposed parallel to said base member.

8. The apparatus according to claim 7 where each wall of said one pair of opposed walls is provided with a central slot and a pair of lateral slots disposed on either side of said central slot, wherein each of said covers is provided with a pair of spaced apart and generally parallel gear sectors and an outwardly extending tab disposed between and spaced from said pair of gear sectors, wherein said gear sectors are provided with inwardly extending generally radial slots for receiving said axles to mount said gear sectors pivotally to said axles, and wherein said tabs are for being inserted into said central slots to snap-fit said covers to said one pair of opposed walls, wherein upon said tabs being received in said central slots said tabs restraining said covers against lateral movement with respect to said shell and restricting said covers to pivotal movement with respect to said shell, and wherein said gear sectors extend through said lateral slots provided in said one pair of opposed walls upon said gear sectors pivoting about said axles toward each other to cover the used syringe needle.

9. Apparatus according to claim 8 wherein said one pair of opposed walls are provided with lower diagonally disposed wall portions and wherein said diagonally disposed and angularly inclined latching members are provided on said lower diagonally disposed wall portions.

10. The apparatus according to claim 9 wherein one gear sector from said each pair of gear sectors comprise a pair of diagonally disposed gear sectors, wherein said pair of diagonally disposed gear sectors are engaged by said latching members and wherein said pair of diagonally disposed gear sectors include teeth having a width and wherein said pair of diagonally disposed gear sectors are provided respectively with a toothless gear slot greater in width than the width of said teeth and into which toothless gear slots said latching members extend to lock said covers in said closed position to cover the used syringe needle.

11. The apparatus according to claim 7 wherein said base member has a generally central portion, and wherein said apparatus further comprises a pair of opposed generally tubular members extending outwardly and oppositely from said central portion of said base member, wherein one of said tubular portions extending outwardly within said rectangular walls and being formed in the shape of a tapered male luer connector for a snap-fit connection with an internally tapered female connection provided on the syringe needle, wherein the other of said tubular portions is formed in the shape of an internally tapered female luer connector having an outer portion provided with a pair of opposed lugs for a locking fitting connection with a tapered male luer connector and an internally threaded collar provided on a syringe, and wherein said tubular portions and said base member are provided with a generally centrally formed internal passageway extending therethrough for placing the syringe and the syringe needle in fluid communication.

12. The apparatus according to claim 3 wherein said base means and said covers are provided with cooperative snap-fit means for snap-fitting said covers to said base means.

13. The apparatus according to claim 12 wherein said cooperative snap fit means restrain said covers against lateral movement with respect to said base means and restrict said covers to pivoting movement with respect to said base means.

14. The apparatus according to claim 13 wherein said cooperative snap fit means comprise a pair of cantilevered tabs provided on said covers and a pair of opposed openings provided on said base means and wherein said cantilevered tabs extend into said openings to snap-fit said covers to said base means.

15. Apparatus for use with a syringe and syringe needle and for covering the syringe needle after use, comprising:

a base for being connected to the syringe and the syringe needle, said base provided with a liquid passageway for communicating liquid from the syringe to the syringe needle;

a pair of covers mounted pivotally to said base and for being pivoted towards each other into a closed position covering the syringe needle after use, each cover provided with a gear in engagement with the gear provided on the other cover making the pivoting movement of each cover dependent on the pivoting movement of the other cover; and a pair of diagonally disposed and angularly inclined latching members provided on said base, each latching member for engaging a gear provided on a different one of said covers to cause either or both of said latching members to limit the pivoting movement of said covers to pivoting movement towards each other into said closed position and to lock both of said covers in said closed position.

16. Apparatus for covering a used syringe needle, comprising:

a base;

a first cover and a second cover, said first cover provided with a first gear sector and a second gear sector, said first gear sector and said second gear sector being spaced apart and generally parallel, said second cover provided with a third gear sector and a fourth gear sector, said third gear sector and said fourth gear sector being spaced apart and generally parallel, said gear sectors mounted pivotally to said base to provide pivoting movement to said covers towards each other into a closed position to cover the used syringe needle, said first gear sector engaging said third gear sector, and said second gear sector engaging said fourth gear sector to make the pivoting movement of said covers dependent on each other due to said engagement of said gear sectors; and a first latching member and a second latching member, said first latching member and said second latching member being disposed diagonally on said base and angularly inclined with respect to said base, said first latching member engaging said first gear sector and said second latching member engaging said fourth gear sector to cause said latching members to cause said first latching member and said second latching member to lock both of said covers in said closed position due to said engagement between said gear sectors and to cause either of said latching members in the absence of the other latching member to lock both of said covers in said closed position due to said engagement of said gear sectors.

17. The apparatus according to claim 16 wherein said covers are generally longitudinally extending triangularly shaped covers tapering inwardly outwardly with respect to said base, said covers being generally semi-circular in transverse cross-section to cooperatively provide in combination a generally longitudinally extending cavity for receiving the used syringe needle upon said covers being moved into said closed position.

18. The apparatus according to claim 17 wherein said covers meet in a substantially line engagement upon said covers being pivoted into said closed position to cover the used syringe needle, and wherein said covers are respectively provided with alternately disposed inwardly extending flanges for substantially covering said line engagement upon said covers being pivoted into said closed position to provide further cover to the used syringe needle.

19. Apparatus for use with a syringe and syringe needle and for covering the syringe needle after use, comprising:

base means for being connected to the syringe and the syringe needle and provided with a liquid passageway for placing the syringe and the syringe needle in fluid communication;

a pair of covers, each cover including a pair of gear sectors in engagement with the pair of gear sectors provided on the other cover, said pairs of gear sectors opposite to and engaged with each other and mounted pivotally to said base means to permit said covers to be pivoted towards each other into a closed position covering the syringe needle after use; and a pair of diagonally disposed and angularly inclined latching members provided in said base means, each latching member in engagement with one gear sector of each of said pairs of gear sectors, and said latching members for providing uni-directional pivoting movement to said covers towards each other and for locking said covers in said closed position covering the syringe needle after use.

20. Apparatus for use with a syringe and syringe needle and for covering the syringe needle after use, comprising:

a base for being connected to the syringe and the syringe needle and provided with a liquid passageway for placing the syringe and the syringe needle in fluid communication;

a pair of normally open covers and a paid of gear sectors, each pair of gear sectors provided on one of said covers and said pairs of gear sectors being engaged, said covers mounted pivotally to said base by said pairs of gear sectors and for being pivoted towards each other into a closed position covering the syringe needle after use, the pivoting movement of each cover being dependent on the pivoting movement of the other cover due to said engagement of said pairs of gear sectors; and a pair of diagonally disposed and angularly inclined latching members provided in said base, each latching member in engagement with one gear sector of each of said pairs of gear sectors, said latching members for limiting the pivoting movement of said covers to uni-directional pivoting movement towards each other and for locking said covers in said closed position covering the syringe needle after use, and in the absence of either latching member the other latching member, due to said pairs of gear sectors being engaged, for limiting the pivoting movement of said covers to said uni-directional pivoting movement and for locking both of said covers in said closed position.

* * * * *